(12) United States Patent
Chang et al.

(10) Patent No.: US 10,578,571 B2
(45) Date of Patent: Mar. 3, 2020

(54) 3D MICRO AND NANOHEATER DESIGN FOR ULTRA-LOW POWER GAS SENSORS

(71) Applicant: International Business Machines Corporation, Armonk, NY (US)

(72) Inventors: Josephine B. Chang, Ellicott City, MD (US); Hendrik F. Hamann, Yorktown Heights, NY (US); Siyuan Lu, Yorktown Heights, NY (US); Xiaoyan Shao, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/035,789

(22) Filed: Jul. 16, 2018

(65) Prior Publication Data

US 2018/0321172 A1 Nov. 8, 2018

Related U.S. Application Data

(62) Division of application No. 14/955,486, filed on Dec. 1, 2015, now Pat. No. 10,041,898.

(51) Int. Cl.
*G01N 27/12* (2006.01)
*H05B 3/12* (2006.01)
*G01R 3/00* (2006.01)
*G01N 33/00* (2006.01)

(52) U.S. Cl.
CPC ....... *G01N 27/123* (2013.01); *G01N 33/0027* (2013.01); *G01R 3/00* (2013.01); *H05B 3/12* (2013.01); *H05B 2214/04* (2013.01)

(58) Field of Classification Search
CPC ............. G01N 27/123; G01N 33/0027; G01N 27/4077; G01N 27/12; G01N 27/407; H05B 2214/04; H05B 3/12; G01R 3/00
USPC .................. 73/31.05, 31.02, 31.03; 29/592.1
See application file for complete search history.

(56) References Cited

U.S. PATENT DOCUMENTS

| 4,627,269 A | 12/1986 | Forster et al. |
| 5,635,628 A | 6/1997 | Fleischer et al. |
| 5,759,493 A * | 6/1998 | Raisanen ............... G01N 27/12 422/83 |
| 5,767,388 A | 6/1998 | Fleischer et al. |
| 5,866,800 A | 2/1999 | Park et al. |
| 8,443,647 B1 | 5/2013 | Kolmakov et al. |
| 8,490,467 B2 | 7/2013 | Pratt |

(Continued)

OTHER PUBLICATIONS

Karion et al., "Methane emissions estimate from airborne measurements over a western United States natural gas field," Geophysical Research Letters, vol. 40, pp. 1-5 (Aug. 2013).

(Continued)

*Primary Examiner* — John Fitzgerald
*Assistant Examiner* — Truong D Phan
(74) *Attorney, Agent, or Firm* — Vazken Alexanian; Michael J. Chang, LLC

(57) ABSTRACT

High-efficiency, ultra-low power gas sensors are provided. In one aspect, a gas detector device is provided which includes: at least one gas sensor having a plurality of fins; a conformal resistive heating element on the fins; a conformal barrier layer on the resistive heating element; and a conformal sensing layer on the barrier layer. A method of forming a gas sensor as well as a method for use thereof in gas detection are also provided.

18 Claims, 6 Drawing Sheets

(56) References Cited

U.S. PATENT DOCUMENTS

| | | | |
|---|---|---|---|
| 8,691,609 | B1 | 4/2014 | Smith et al. |
| 9,027,387 | B2 | 5/2015 | Blackburn et al. |
| 2006/0154401 | A1* | 7/2006 | Gardner ............... G01N 27/128 438/53 |
| 2009/0145220 | A1 | 6/2009 | Langenbacher et al. |
| 2009/0249859 | A1 | 10/2009 | Takahashi |
| 2011/0163313 | A1 | 7/2011 | Seacrist |
| 2011/0302991 | A1* | 12/2011 | Pratt ..................... G01N 27/16 73/23.2 |
| 2012/0161790 | A1 | 6/2012 | Smith et al. |
| 2013/0036811 | A1* | 2/2013 | Boult ..................... E21B 49/08 73/152.27 |
| 2013/0249022 | A1 | 9/2013 | Du et al. |
| 2013/0264660 | A1 | 10/2013 | Fleischer et al. |
| 2013/0285682 | A1 | 10/2013 | Biskupski et al. |
| 2014/0208828 | A1 | 7/2014 | Von Waldkirch |
| 2015/0090043 | A1 | 4/2015 | Ruhl et al. |
| 2015/0233851 | A1* | 8/2015 | Zan ..................... H01L 51/0001 73/31.06 |
| 2016/0313288 | A1 | 10/2016 | Theuss et al. |
| 2016/0334359 | A1 | 11/2016 | Kim et al. |
| 2017/0003238 | A1 | 1/2017 | Salvador et al. |
| 2017/0102353 | A1 | 4/2017 | Lei et al. |
| 2017/0153198 | A1 | 6/2017 | Chang et al. |

OTHER PUBLICATIONS

J. Peischl et al., "Quantifying sources of methane using light alkanes in the Los Angeles basin, California," Journal of Geophysical Research: Atmospheres, vol. 118, pp. 4974-4990 (May 2013).

Overstolz et al., "A Clean Wafer-Scale Chip-Release Process Without Dicing Based on Vapor Phase Etching," 17th IEEE International Conference on Micro Electro Mechanical Systems, pp. 717-720 (2004).

Chakraborty et al., "Selective Detection of methane and butane by temperature modulation in iron doped tin oxide sensors," Sensors and Actuators B: Chemical, vol. 115, issue 2, pp. 610-613 (Jun. 2006).

L. Xu et al., "Design, Fabrication, and Characterization of a High-Heating-Efficiency 3-D Microheater for Catalytic Gas Sensors," Journal of Microelectromechanical Systems, vol. 21, No. 6, Dec. 2012, pp. 1402-1409.

S.E. Moon et al., "Semiconductor-Type MEMS Gas Sensor for Real-Time Environmental Monitoring Applications," Etri Journal, vol. 35, No. 4, Aug. 2013, pp. 617-624.

M. Graf et al., "Smart single-chip CMOS microhotplate array for metal-oxide-based gas sensors," 12th International Conference on Transducers, Solid-State Sensors, Actuators and Microsystems, vol. 1, Jun. 2003, pp. 123-126.

List of IBM Patents or Applications Treated as Related (2 pages).

* cited by examiner

*FIG.* 12
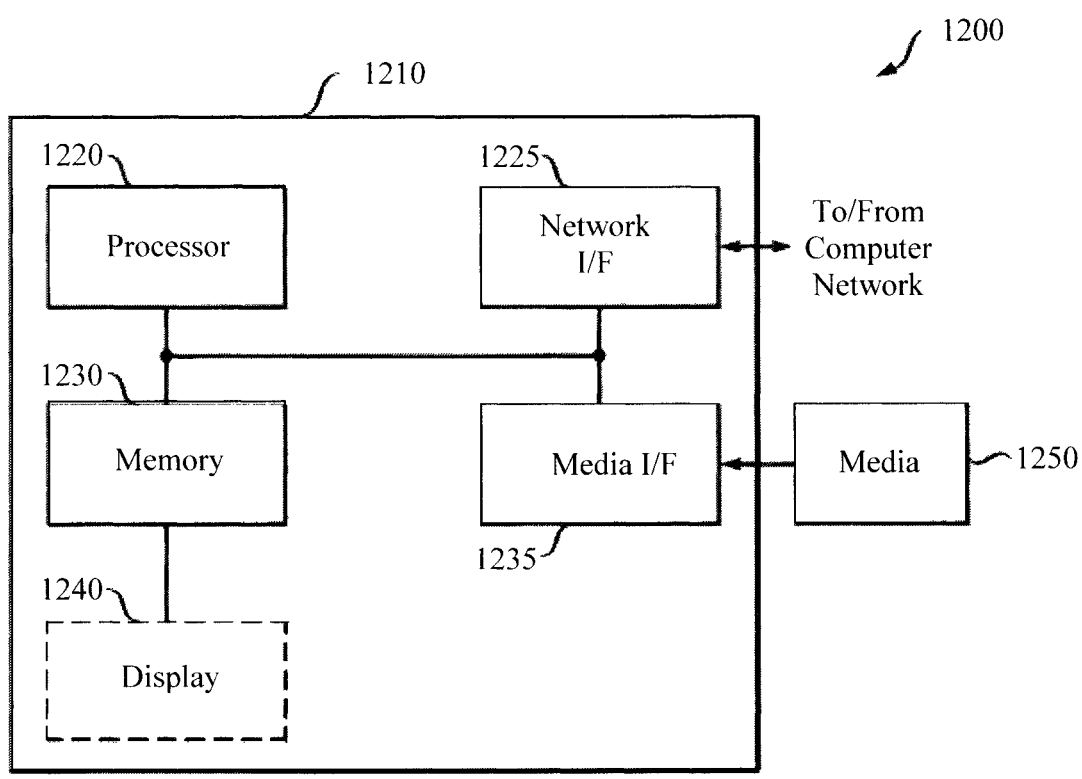

US 10,578,571 B2

3D MICRO AND NANOHEATER DESIGN FOR ULTRA-LOW POWER GAS SENSORS

CROSS-REFERENCE TO RELATED APPLICATION(S)

This application is a divisional of U.S. application Ser. No. 14/955,486 filed on Dec. 1, 2015, now U.S. Pat. No. 10,041,898, the disclosure of which is incorporated by reference herein.

FIELD OF THE INVENTION

The present invention relates to gas sensors, and more particularly, to high-efficiency, ultra-low power gas sensors.

BACKGROUND OF THE INVENTION

There is a great need for portable low power volatile organic compound (VOC) sensors for monitoring VOC emission in today's industrial scale natural gas production. See, for example, Karion et al., "Methane emissions estimate from airborne measurements over a western United States natural gas field," Geophysical Research Letters, vol. 40, pgs. 1-5 (August 2013) and J. Peischl et al., "Quantifying sources of methane using light alkanes in the Los Angeles basin, California," Journal of Geophysical Research: Atmospheres, vol. 118, pgs. 4974-4990 (May 2013).

Semiconductor metal oxide based gas sensors have great potential in such applications due to their low cost and portability. However, the power consumption of such sensors is relatively high (e.g., greater than 50 mW), which hinders their application in continuous monitoring with battery power in a service time scale of years. For instance, microelectromechanical (MEMS)-based membrane gas sensors, which are currently the most advanced and of the lowest power consumption, still consume from about 6 mW to about 20 mW of power. The high power consumption of these sensors is mainly due to the requirement of operating the sensors at elevated temperatures (e.g., from about 300° C. to about 400° C.) during gas sensing in order to achieve reasonable sensitivity.

Therefore, improved low-power gas sensors would be desirable.

SUMMARY OF THE INVENTION

The present invention provides high-efficiency, ultra-low power gas sensors. In one aspect of the invention, a gas detector device is provided. The gas detector device includes: at least one gas sensor having a plurality of fins; a conformal resistive heating element on the fins; a conformal barrier layer on the resistive heating element; and a conformal sensing layer on the barrier layer.

In another aspect of the invention, a method of forming a gas sensor is provided. The method includes the steps of: patterning a plurality of fins in a substrate; depositing a conformal resistive heating element on the fins; depositing a conformal barrier layer on the resistive heating element; and depositing a conformal sensing layer on the barrier layer.

In yet another aspect of the invention, a method of gas detection is provided. The method includes the steps of: providing a gas detector device having at least one gas sensor that includes: a plurality of fins; a conformal resistive heating element on the fins; a conformal barrier layer on the resistive heating element; and a conformal sensing layer on the barrier layer; heating the gas sensor via the resistive heating element; and taking readings from the gas sensor.

A more complete understanding of the present invention, as well as further features and advantages of the present invention, will be obtained by reference to the following detailed description and drawings.

BRIEF DESCRIPTION OF THE DRAWINGS

FIG. 12 is a diagram illustrating an exemplary apparatus for performing one or more of the present methodologies according to an embodiment of the present invention.

DETAILED DESCRIPTION OF PREFERRED EMBODIMENTS

Figure 1:
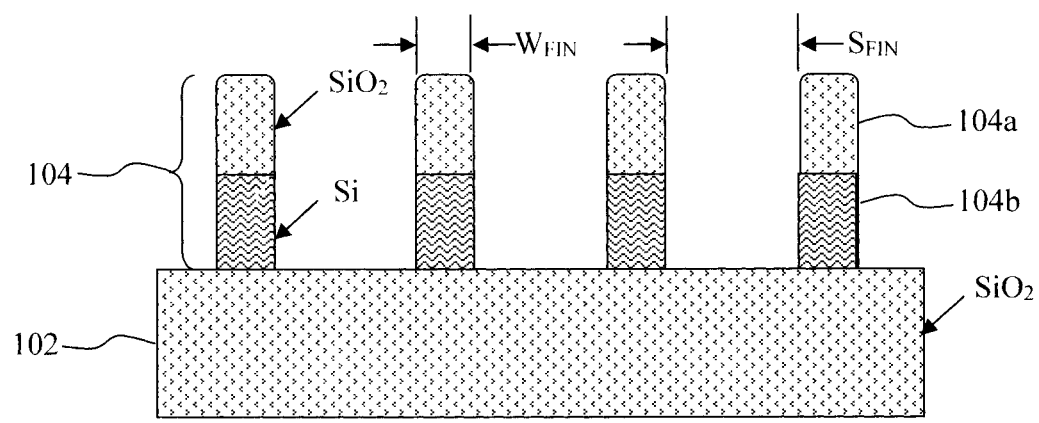
FIG. 1 is a cross-sectional diagram illustrating a plurality of fins having been patterned in a substrate according to an embodiment of the present invention.
Figure 2:
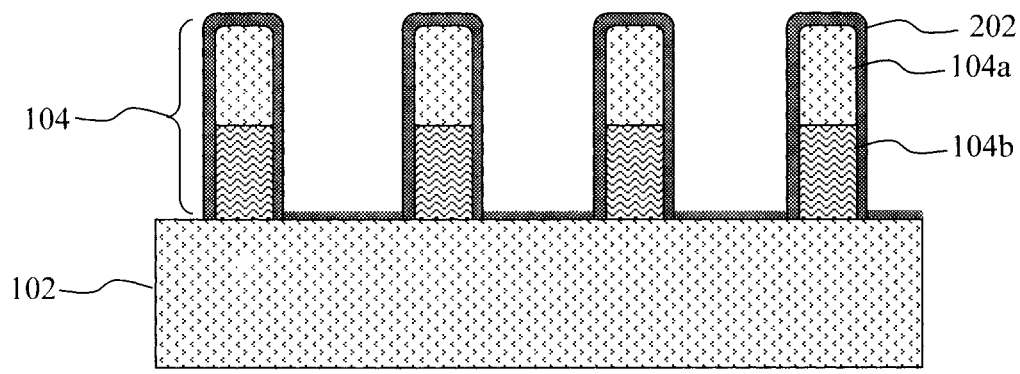
FIG. 2 is a cross-sectional diagram illustrating a resistive heating element having been formed on the fins according to an embodiment of the present invention.
Figure 3:
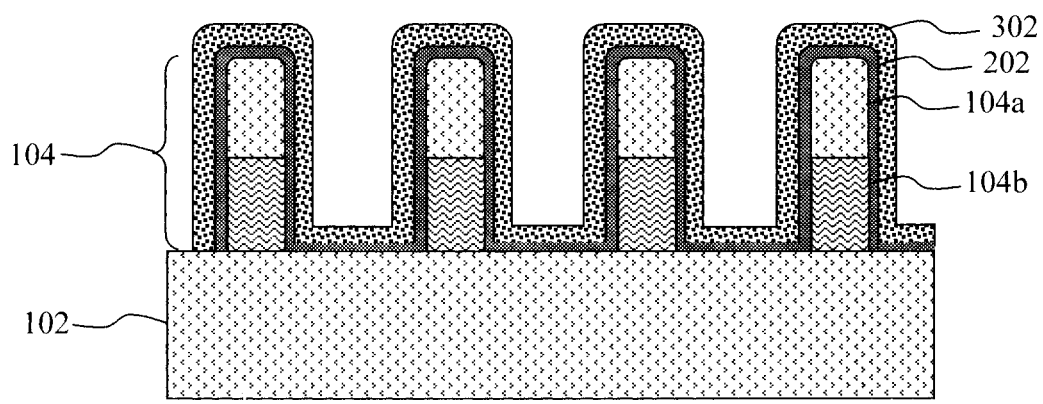
FIG. 3 is a cross-sectional diagram illustrating a thin barrier layer having been deposited onto the resistive heating element according to an embodiment of the present invention.

As provided above, a significant drawback to current gas sensor technology is a relatively high power consumption, which limits their long term use in the field. Advantageously, provided herein are new innovative gas sensor designs which can achieve 100× reduction in power consumption as compared with conventional sensors.

The typical gas sensor on the market today uses ceramic or glass substrates to benefit from the low thermal conductivity of these materials. However, the heated area is relatively large: in hundreds of microns to over several millimeters in linear dimensions. There have also been efforts to try to build gas sensors on silicon substrates to utilize complementary metal-oxide semiconductor (CMOS) technology. An example of such sensors is microelectromechanical (MEMS)-based membrane gas sensors. See, for example, U.S. Patent Application Publication Number 2015/0090043 by Ruhl et al., entitled "MEMS." There are, however, three key drawbacks of the MEMS based sensor design. First, the high thermal conductivity of the silicon (Si) substrate makes it hard to achieve power reduction due to the large amount of thermal loss through the substrate. Second, due to the chemical wet etch process limitations, a relatively large size heater is produced (several hundreds of micrometers). Third, the mechanical strength of the membrane in portable sensors is a concern.

The full potential of battery-powered gas sensors cannot be fulfilled without the successful scaling of the heater down to a few micrometers or submicron dimensions either on silicon substrate or on ceramic/glass substrates. In the present sensor design, the heater size and the sensor dimensions are substantially reduced down to micrometer scale (less than 10 micrometers in size) and even nanometer.

Advantageously, the present design can reduce power consumption substantially in three aspects. First, according to an exemplary embodiment, the commonly used Si substrate is replaced with the same thickness of silicate glass wafers. The thermal conductivity of borosilicate glass is about 1.1 watts per meter Kelvin (W/m·K). This alone can reduce heat loss of the substrate by about 100× (as compared to Si) without compromising the mechanical strength of the substrate. According to another exemplary embodiment, low thermal conductivity on silicon is achieved by creating air pockets or pores inside the silicon substrate using a dry etch process.

Second, as will be described in detail below, the heating element is woven inside the sensor fins in order to maximize heat utilization by closely patterning the fins. In this manner, the sensing area is increased by a factor of from about 5 to about 10 times for the same area of substrate. To put it in another way, heat dissipation through the substrate is reduced by a factor from about 5 to about 10 times with the same amount of tin oxide ($SnO_2$) sensing surface as compared with a planar layout.

Third, according to an exemplary embodiment, a serpentine layout is used for the fins. A serpentine layout can scale down the dimension of total sensing area without compromising resistive path length of the sensing materials. This opens the door for miniaturization of sensors and enables array fabrication without significant cost increase.

An exemplary process for fabricating the present gas sensor is now described by way of reference to FIGS. 1-7. As shown in FIG. 1, the process begins with a substrate 102 in which a plurality of fins 104 is patterned. According to an exemplary embodiment, the starting platform for the process is a silicon-on-insulator (SOI) wafer. As is known in the art, a SOI wafer includes a SOI layer separated from a substrate (e.g., a silicon (Si) substrate) by a buried insulator. The buried insulator can include, for example, an oxide, such as a silicon dioxide ($SiO_2$). When the buried insulator is an oxide, it is commonly referred to as a buried oxide or BOX. In this example, the fins 104 are patterned by first forming a plurality of fin masks 104a on the SOI layer. According to an exemplary embodiment, the fin masks 104a are formed from an insulator such as $SiO_2$ (see FIG. 1) or silicon nitride (SiN). The fin masks 104a can be formed by directly patterning a suitable mask material or, optionally, a pitch-doubling technique such as sidewall image transfer (SIT) may be employed. SIT generally involves forming one or more mandrels on a substrate, forming spacers on opposite sides of the mandrel(s), removing the mandrel(s) selective to the spacers, and then using the spacers to pattern the substrate. An advantage to SIT is that it permits patterning features at a sub-lithographic pitch. The spacers too may be formed from an insulator such as $SiO_2$ or SiN.

Standard lithography and etching techniques can then be used to pattern the SOI layer, via the fin masks 104a, into individual fin portions 104b. In this example, the fin masks 104a and the patterned SOI layer portions 104b are what form the fins 104. As highlighted above, a buried insulator is present beneath the SOI layer. Thus, in this exemplary embodiment, the substrate 102 shown in FIG. 1 would be the buried insulator (e.g., $SiO_2$).

The process is, however, not limited to SOI wafer configurations. For instance, in the same manner described, the fins 104 can be patterned in a bulk semiconductor (e.g., a bulk Si wafer). To isolate the fins, an insulator (such as $SiO_2$) can be deposited or grown on the fins, thereby forming the fin configuration shown in the figures, i.e., having an $SiO_2$ portion 104a and an Si portion 104b.

As will be apparent from the following description, the purpose of the fins 104 is to provide a template on which a plurality of gas sensors is built. Building the sensor on a high-aspect ratio fin structure greatly increases the surface area and thereby the sensitivity of the sensors without increasing the overall sensor footprint. According to an exemplary embodiment, the fins each have a width ($W_{FIN}$) of from about 20 nanometers (nm) to about 100 nm, and ranges therebetween, and a fin-to-fin spacing ($S_{FIN}$) of from about 50 nm to about 150 nm, and ranges therebetween.

A resistive heating element 202 is then formed on the fins 104. See FIG. 2. According to an exemplary embodiment, the resistive heating element 202 is formed from a thin conformal layer of a metal, such as tantalum nitride (TaN), titanium nitride ($TiN_x$), tungsten (W), and other resistive metals or compounds containing at least one of the foregoing metals, using a process such as evaporation or sputtering, to a thickness of from about 3 nanometers (nm) to about 10 nm, and ranges therebetween.

A thin barrier layer 302 is next deposited onto the resistive heating element 202. See FIG. 3. According to an exemplary embodiment, the barrier layer 302 is formed from a thin conformal layer of a nitride material such as silicon nitride (SiN), silicon oxide ($SiO_x$), alumina, other insulating oxides or nitrides, or combinations thereof, using a process such as chemical vapor deposition (CVD) or atomic layer deposition (ALD), to a thickness of from about 1.5 nm to about 3 nm, and ranges therebetween.

A sensing layer 402 is then deposited onto the barrier layer 302. See FIG. 4. The type of sensing layer used depends on the gas being detected. By way of example only, tin oxide ($SiO_2$)-based sensors are sensitive to a variety of different gases, such as methane ($CH_4$), hydrogen sulfide ($H_2S$), sulfur dioxide ($SO_2$), carbon monoxide (CO), etc. Zinc oxide (ZnO)-based sensors are sensitive to gases such as oxygen ($O_2$), carbon dioxide ($CO_2$), and hydrogen ($H_2$). Thus, according to an exemplary embodiment, the sensing layer 402 is formed from $SnO_2$, ZnO, or a mixture thereof, e.g., zinc tin oxides. The resistance through a $SnO_2$, ZnO, or zinc tin oxide sensing layer changes when exposed to a particular gas or gasses. Generally, during operation, a $SnO_2$, ZnO, or zinc tin oxide gas sensor is heated to a temperature of greater than about 300° C. (e.g., from about 300° C. to about 600° C., and ranges therebetween)—since at room temperature, no reaction will occur. When the heated sensor is exposed to one of the above gases, the resistance through the sensing layer will drop. Thus by monitoring the resistance of the sensing layer, the presence of the gas can be easily detected. The amount by which the resistance changes is dependent on several different factors. For instance, as provided above, a $SnO_2$, ZnO, or zinc tin oxide sensing layer reacts with a variety of different gases. However, the temperature at which the reaction occurs varies depending on the gas. Thus, one can control the temperature to control which gases the sensor is sensitive to. Also, the amount by which a given gas reacts with a given sensing layer varies depending on the gas. Thus, for a given temperature, one can also detect the presence of different gases based on the resistance changes in the sensing layer.

As provided above, one important design consideration contemplated herein is to be able to reduce power consumption of the sensors by reducing the amount of heat conducted through the substrate. Namely, if the substrate acts as a significant thermal conductor, then a greater amount of heat needs to be generated (i.e., by the resistive heating element) to achieve a given temperature, which in turn uses more power. A few different techniques are anticipated herein for reducing the thermal conductivity of the sensor substrate.

Figure 4:
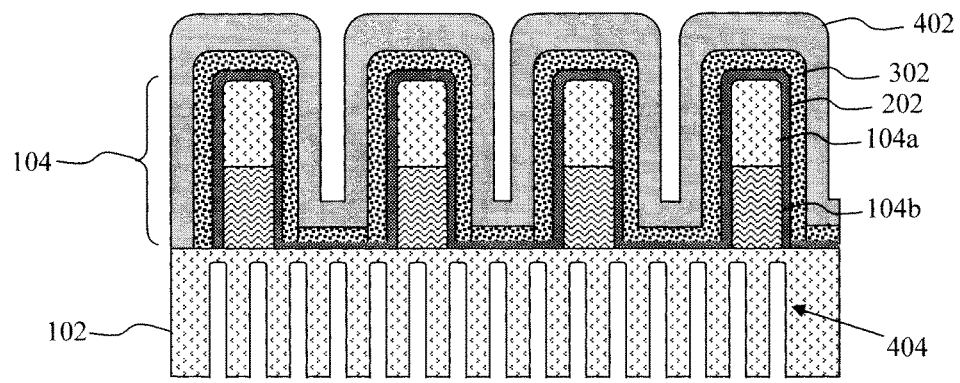
FIG. 4 is a cross-sectional diagram illustrating a sensing layer having been deposited onto the barrier layer, and optional air pockets or pores having been formed in the substrate to reduce thermal conductivity according to an embodiment of the present invention.

In a first exemplary embodiment, the thermal conductivity of the substrate 102 is reduced by creating air pockets 404 in the substrate 102. See, for example, FIG. 4. The concept here is that the thermal conductivity of air is orders of magnitude less than that of the (e.g., $SiO_2$) substrate. Thus, by creating pockets of air in the substrate 102, its overall thermal conductivity will be reduced (as compared with a substrate 102 without such air pockets). The air pockets 404 can be created in the substrate 102 using a standard dry etching process, such as deep plasma etching. As shown in FIG. 4, the air pockets are etched from the backside of the substrate 102 and extend almost through the substrate 102. One skilled in the art would be able to control a plasma etching process to create such vias in a substrate that extend part way through the substrate.

Figure 5:
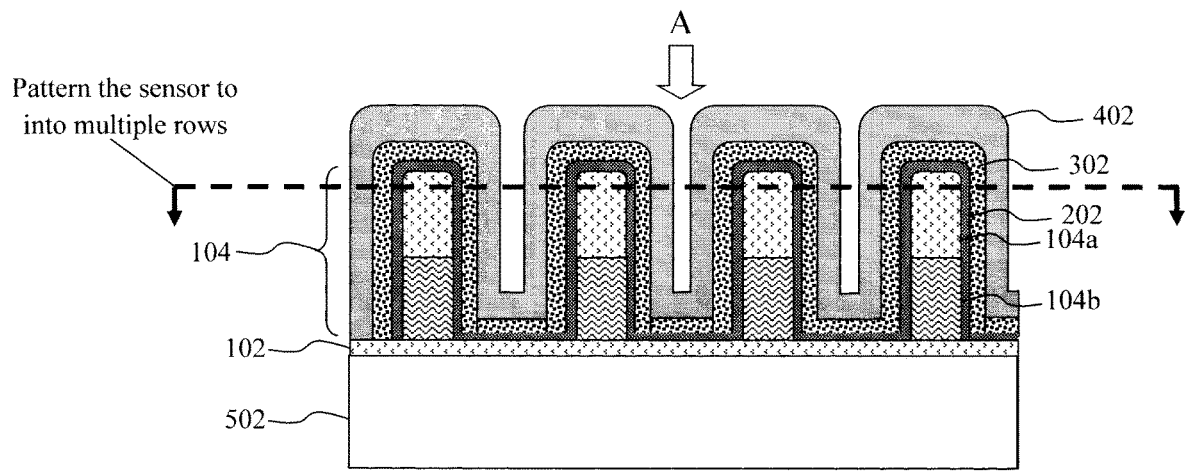
FIG. 5 is a cross-sectional diagram illustrating the completed sensor optionally having been detached from the substrate and reattached to a different, low-K substrate according to an embodiment of the present invention.

Another technique anticipated herein for reducing the thermal conductivity of the substrate is to detach the completed sensor from the bulk of substrate 102 and attach it to a low-κ substrate 502, such as a ceramic or borosilicate glass substrate. Backside polishing, spalling, vapor phase etching, or chemical etching methods can be used to detach the sensors from the bulk silicon substrate. See FIG. 5. As provided above, the thermal conductivity of borosilicate glass is about 1.1 W/m·K. Any technique known in the art for releasing a device from the bulk of a substrate may be employed. See, for example, Overstolz et al., "A Clean Wafer-Scale Chip-Release Process Without Dicing Based on Vapor Phase Etching," 17th IEEE International Conference on Micro Electro Mechanical Systems, pgs. 717-720 (2004)," the contents of which are incorporated by reference as if fully set forth herein. As shown in FIG. 5, a portion of the original substrate 102 preferably remains in place to provide mechanical support during the substrate transfer process.

According to an exemplary embodiment, a serpentine layout of the gas sensors is employed. By "serpentine," it is meant that the gas sensor includes multiple interconnected rows of the resistive heating element 202/barrier layer 302/sensing layer 402. For instance, as will be described in detail below, in one example, the resistive heating element 202 in two adjacent rows is connected at one end of the rows. The resistive heating element 202 is connected to the next adjacent row at the opposite end, and so on, forming a serpentine layout of interconnected rows. This serpentine layout serves to balance two important design considerations, one being minimizing power consumption, and the other maximizing sensor sensitivity. With regard to minimizing power consumption—by having the heating element and sensing layer divided into distinct interconnected rows (rather than, e.g., a single heater/sensing layer over the entire footprint of the sensor), the total area of the sensing layer needing to be heated is reduced, thereby reducing the overall power consumption. However, with the serpentine layout, the sensing layer is still present across the entire footprint of the sensor, thereby maximizing sensitivity.

Figure 6:
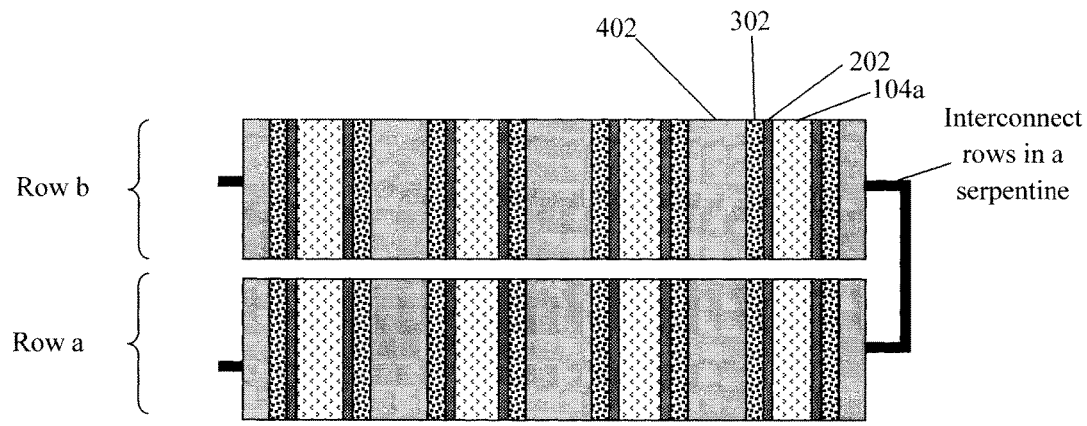
FIG. 6 is a top-down diagram of the structure of FIG. 5 following the sensor having been patterned into a plurality of parallel, interconnected rows, forming a serpentine sensor layout according to an embodiment of the present invention.

This serpentine layout can be achieved in a number of different ways. For instance, according to one exemplary embodiment, the sensor can be built in the manner described above. Following deposition of the sensing layer 402, the sensor can then be divided into a plurality of distinct rows. For instance, standard lithography and etching techniques can be used to divide the fins and sensor structure into multiple parallel rows. See, for example, FIG. 6. FIG. 6 is a top-down view of the structure of FIG. 5 (i.e., from a viewpoint A) following the fins and sensor structure having been patterned into a plurality of parallel rows a, b, etc. For clarity, the top of the structure has been removed in FIG. 6 so that the various device layers are visible. As shown in FIG. 6, the patterning in this case extends down through the fins 104 such that each fin is divided into two or more separate rows of the sensor. An arrow is provided in FIG. 5 to indicate the orientation of the cut through the fins/sensor structure to form the rows depicted in FIG. 6.

To form the serpentine layout, each of the patterned rows is interconnected. See FIG. 6. According to an exemplary embodiment, a wire or other electrically conductive conduit is used to connect the resistive heating element 202 in adjacent rows, forming a continuous resistive heating path throughout the sensor. Thus, for instance, if the sensor is patterned into 10 distinct rows, then one common resistive heating path is created interconnecting each of the 10 rows.

Figure 7:
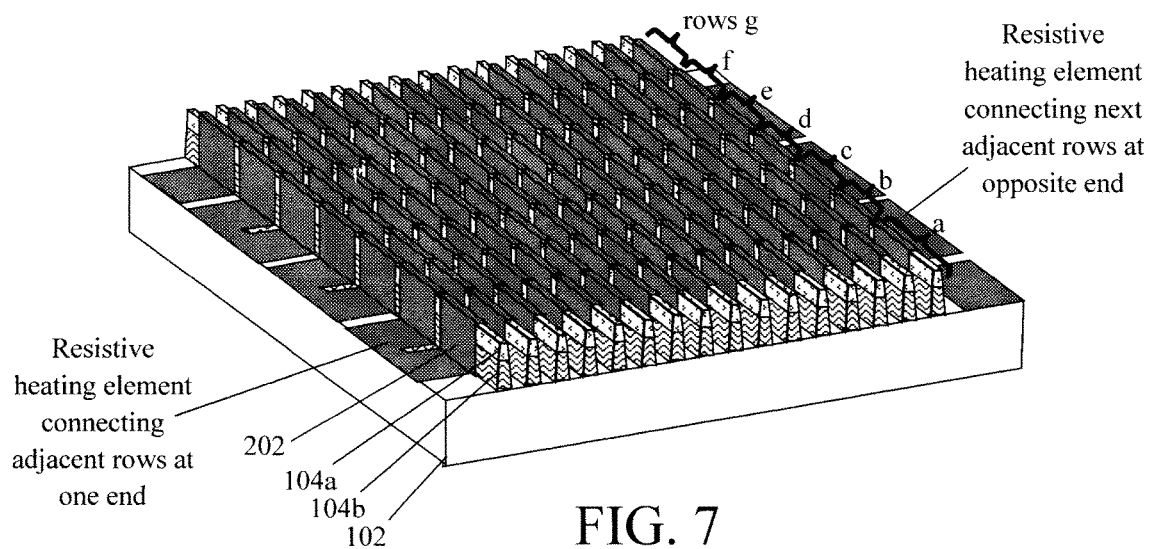
FIG. 7 is a three-dimensional diagram of the present gas sensor oriented as a plurality of parallel rows interconnected by the resistive heating element in a serpentine configuration according to an embodiment of the present invention.

As shown in FIG. 7, the present gas sensor is provided having a serpentine layout. For consistency, like structures with the embodiments described above are numbered alike in the following figures. The sensor shown in FIG. 7 is formed using the above-described process. In this example, the various rows of the serpentine design are interconnected by overlapping portions of the resistive heating element 202 that connect adjacent rows. In particular, as shown in FIG. 7, the resistive heating element 202 interconnects two adjacent rows at one end, and the next adjacent rows at the opposite ends thereby forming a serpentine design.

Figure 8:
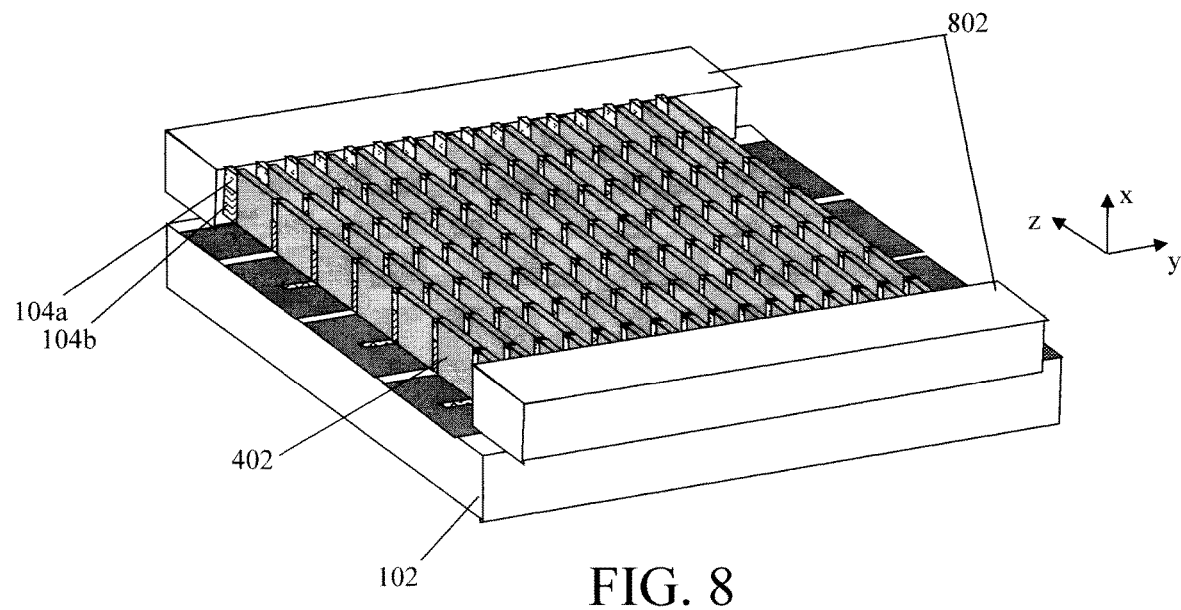
FIG. 8 is a three-dimensional diagram illustrating the barrier layer and sensing layer having been deposited onto the resistive heating element, and sensing electrodes having been formed to complete the sensor according to an embodiment of the present invention.

In the same manner as described above, the barrier layer 302 (not visible) and sensing layer 402 is then deposited onto the resistive heating element 202. See FIG. 8. Standard metallization techniques are then used to form sensing electrodes 802 in contact with the sensing layer 402. The sensing electrodes 802 serve to measure the resistance through the sensing layer 402. In the example shown in FIG. 8, the sensing electrodes 802 are formed on opposite sides of the sensor, parallel to the rows. In other words, the (serpentine) interconnected rows (i.e., rows a-g, see FIG. 7) run along a y-axis. The rows are adjacent to one another on the z-axis. The sensing electrodes 802 are present on opposite ends of the sensor (along the z-axis). The fins increase the sensing area along the x-axis (without increasing the overall sensor footprint—see above).

Figure 9:
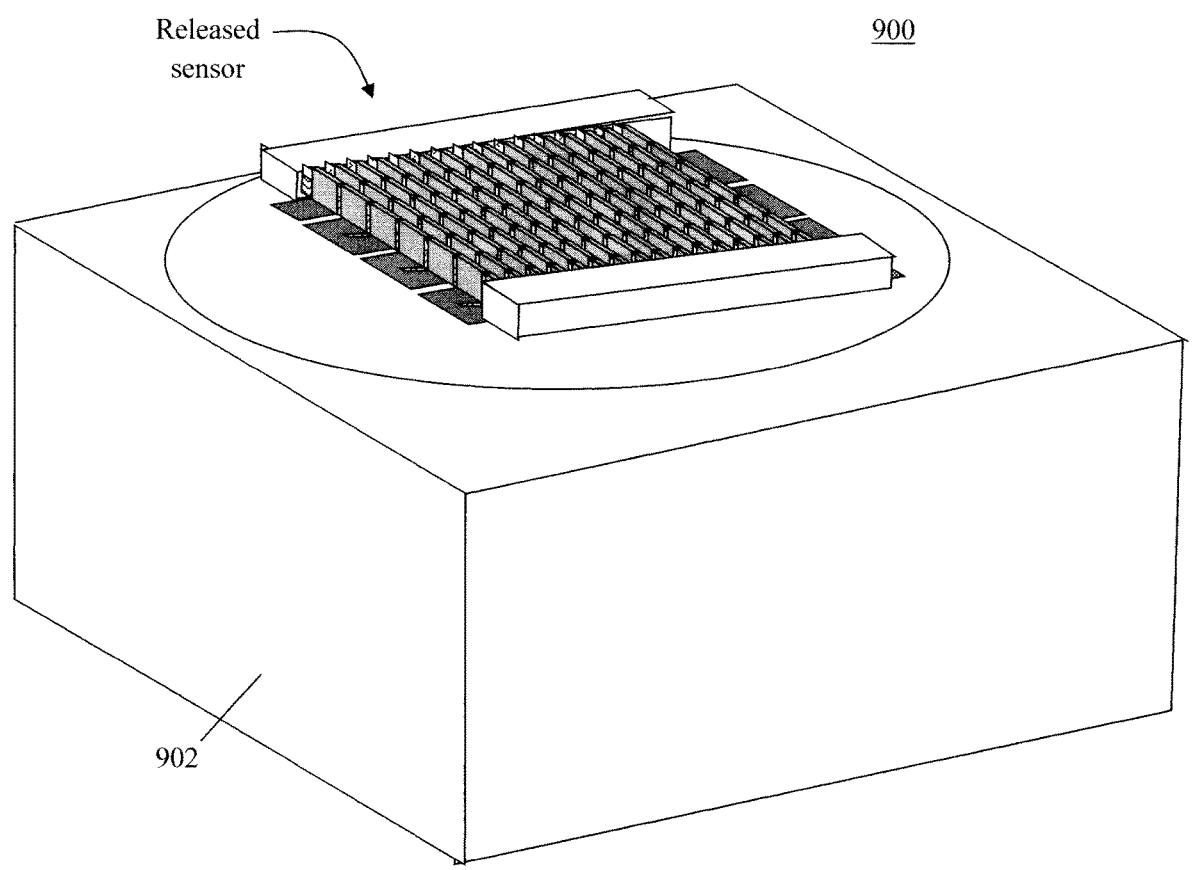
FIG. 9 is a three-dimensional diagram illustrating the sensor having been transferred to a low-K substrate according to an embodiment of the present invention.

As described above, one technique anticipated herein for reducing the overall thermal conductivity of the substrate is to release the sensor from its original substrate and transfer the sensor to a low-K substrate (e.g., low-K substrate 902), such as a ceramic or borosilicate glass substrate. See FIG. 9.

As will be described in detail below, an array of the present sensors (as shown, for example, in FIGS. 7-10) can provide several notable benefits. First, an array provides a degree of redundancy. For instance, environmental factors in the field, such air current, wind etc. can affect the presence, concentration, etc. of a gas being detected. In windy conditions, the gas might pass undetected over a single sensor. However, by employing an array of sensors over which the gas passes, there is a greater chance that the gas will be detected by at least some of the sensors in the array. Further, using multiple sensors (i.e., in an array) can also provide data useful in pinpointing the source of the gas. For instance, assuming the orientation of the sensor array is known, then the gas passing over the array will first be detected by the sensors in the array closest to the source, followed by the sensors along the path of travel of the gas flow. Therefore, data collected about which sensors in the array detected the gas and when, one can deduce the path of flow of the gas.

Another notable benefit of an array design is that different sensors (sensitive to different gasses) can be included in the same array, thus making the data collected in the field more comprehensive. For instance, gas leaks can include more than one type of gas. As provided above, the sensitivity of the sensing layer (such as $SnO_2$) to different gasses can vary depending on the temperature at which the sensing layer is operated (via the resistive heating element). Thus, by way of example only, different sensors in the array can be operated at different temperatures, thereby making the array sensitive to a variety of different gases.

The completed sensor 900 may now be used in the field for gas sensing. However, as highlighted above, embodiments are anticipated herein where multiple sensors are arranged as array. As described above, there are notable advantages to an array implementation. For instance, multiple sensors provide a level of redundancy, thereby increasing the overall accuracy of the measurements. Further, the detection of the path of the gas over the sensors in the array can be used to pinpoint the source (e.g., thereby enabling detection of the source of a gas leak, etc.). The array might also include different sensors (i.e., sensors for detecting different gases). In that case, the array can enable detection of different gas species (e.g., in the instance where a gas leak contains multiple gases).

Figure 10:
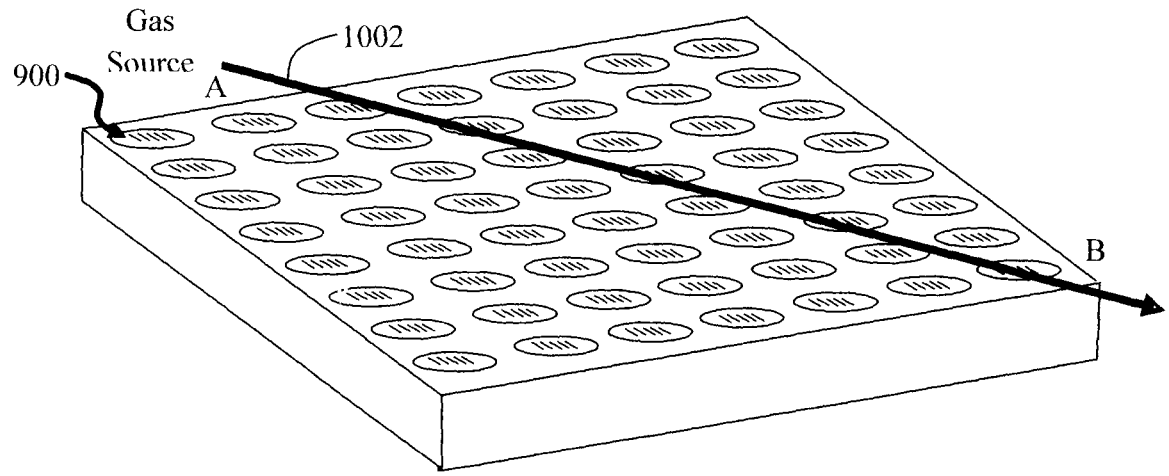
FIG. 10 is a three-dimensional diagram illustrating multiple sensors compiled into an array according to an embodiment of the present invention.

Thus, according to an exemplary embodiment, as shown in FIG. 10 multiple sensors 900 are compiled in an array. In this case, there are 7×8=56 sensors in the array. This is however only an example, and arrays containing more or fewer sensors than shown are contemplated herein. FIG. 10 illustrates one of the above-mentioned advantages of a sensor array. Namely, an arrow 1002 is used to illustrate the path of a gas across the sensor array. As the gas is first detected by the sensor(s) at point A in the array, and then by the sensors along the path from point to point B in the array, it may be assumed that the source of the gas is present (along that path, at its origin).

Figure 11:
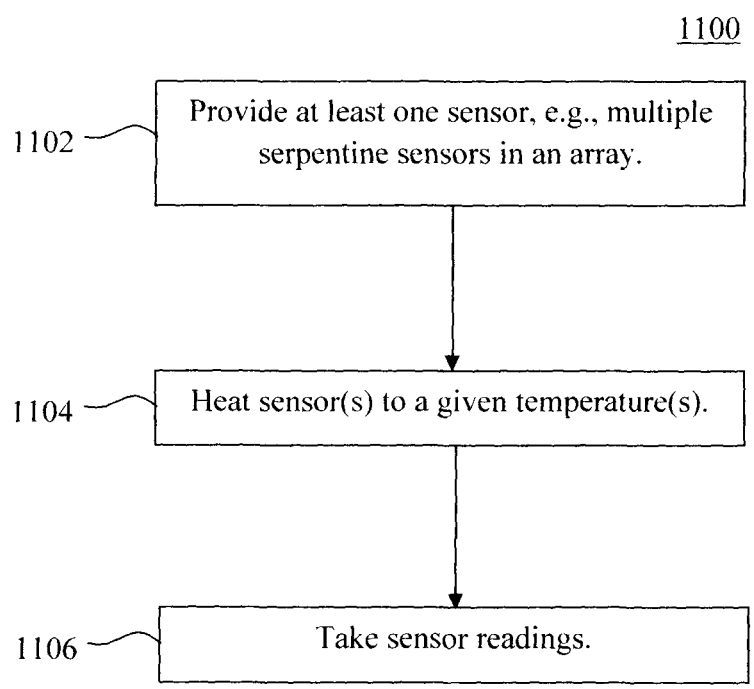
FIG. 11 is a diagram illustrating an exemplary methodology for gas detection using the present gas sensors according to an embodiment of the present invention.

FIG. 11 is a diagram illustrating an exemplary methodology 1100 for gas detection using the present sensors. In step 1102, at least one of the present gas sensors is provided. According to an exemplary embodiment, the gas sensor is configured to have the serpentine layout described above. Further, according to an exemplary embodiment, a plurality of the present gas sensors is present and are arranged in array (see, for example, FIG. 10). Yet further, according to an exemplary embodiment, one or more of the sensors in the array is different from another one or more of the sensors in the array (i.e., the sensors in the array are configured to detect different gases).

In step 1104, the sensing layer 402 in the at least one sensor is heated to a given temperature via the resistive heating element 202. As provided above, the selectivity of the sensor to different gases can vary depending on the sensor temperature. For instance, the ability of a $SnO_2$ sensing layer 402 to detect various gases can be changed simply by varying the temperature of the sensing layer 402. For instance, at a temperature of 350° C. a $SnO_2$ sensor can detect both methane and butane gas however, when the temperature is raised to 425° C., the same sensor is selective to detecting only butane. See, for example, Chakraborty et al., "Selective Detection of methane and butane by temperature modulation in iron doped tin oxide sensors," Sensors and Actuators B: Chemical, vol. 115, issue 2, pgs. 610-613 (June 2006), the contents of which are incorporated by reference as if fully set forth herein.

It is notable that the individual sensors in an array can be independently heated to different temperatures, e.g., so as to regulate their sensitivity to various different gases. Thus, according to an exemplary embodiment, in step 1104 at least one of the sensors in the array is heated to a different temperature from at least one or more other sensors in the array to confer different sensing capabilities across the array.

In step 1106, readings are taken from the sensors. As described in detail above, the resistance of the sensing layer 402 changes when the sensors are exposed to a gas. For instance, in the case of a $SnO_2$ sensing layer, the resistance of the sensing layer changes when the sensor is exposed to a certain gas(es) such as methane. The resistance of the sensing layer 402 can be measured via the sensing electrodes 802. Further, in step 1106, the readings are preferably time stamped (i.e., the time the readings are taken are recorded). As provided above, this will enable detection of the path of the gas across the sensor array. Take for instance the scenario where a gas is detected at times T1, T2, and T3 (wherein T1<T2<T3) at sensors S1, S2, and S3, respectively, in the array. It can be assumed that the path of the gas across the array is along sensors S1, S2, and S3, in that order. One can then trace back the path to approximate the source of the gas. See, for example FIG. 10.

Any data storage, collection and/or processing may be carried out in conjunction with the present gas sensing device, for example, using an apparatus such as that shown in FIG. 12. In FIG. 12, a block diagram is shown of an apparatus 1200 for implementing one or more of the methodologies presented herein. Apparatus 1200 includes a computer system 1210 and removable media 1250. Computer system 1210 includes a processor device 1220, a network interface 1225, a memory 1230, a media interface 1235 and an optional display 1240. Network interface 1225 allows computer system 1210 to connect to a network, while media interface 1235 allows computer system 1210 to interact with media, such as a hard drive or removable media 1250.

Processor device 1220 can be configured to implement the methods, steps, and functions disclosed herein. The memory 1230 could be distributed or local and the processor device 1220 could be distributed or singular. The memory 1230 could be implemented as an electrical, magnetic or optical memory, or any combination of these or other types of storage devices. Moreover, the term "memory" should be construed broadly enough to encompass any information able to be read from, or written to, an address in the addressable space accessed by processor device 1220. With this definition, information on a network, accessible through network interface 1225, is still within memory 1230 because the processor device 1220 can retrieve the information from the network. It should be noted that each distributed processor that makes up processor device 1220 generally contains its own addressable memory space. It should also be noted that some or all of computer system 1210 can be incorporated into an application-specific or general-use integrated circuit.

Optional display 1240 is any type of display suitable for interacting with a human user of apparatus 1200. Generally, display 1240 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method of gas detection, the method comprising the steps of:
    providing a gas detector device having at least one gas sensor comprising: a plurality of fins; a conformal resistive heating element on the fins; a conformal barrier layer on the resistive heating element; and a conformal sensing layer on the barrier layer, wherein the conformal resistive heating element, the conformal barrier layer and the conformal sensing layer each conforms to a shape of the fins thereby providing a plurality of gas sensor layers disposed conformally over the fins with a gap present between the gas sensor layers over adjacent fins, and wherein the gas sensor further comprises a substrate beneath the fins;
    heating the gas sensor via the resistive heating element; and
    taking readings from the gas sensor.

2. The method of claim 1, wherein the substrate comprises a plurality of air pockets.

3. The method of claim 1, wherein the substrate comprises a ceramic or borosilicate glass substrate.

4. The method of claim 1, wherein the resistive heating element comprises a material selected from the group consisting of: tantalum nitride, titanium nitride, tungsten, and combinations thereof.

5. The method of claim 1, wherein the barrier layer comprises a material selected from the group consisting of: silicon nitride, silicon oxide, alumina, and combinations thereof.

6. The method of claim 1, wherein the sensing layer comprises a material selected from the group consisting of: tin oxide, zinc oxide, and combinations thereof.

7. The method of claim 1, wherein the gas sensor comprises multiple rows of the resistive heating element, the barrier layer, and the sensing layer interconnected in a serpentine configuration.

8. The method of claim 1, wherein the gas detector device comprises a plurality of gas sensors arranged in an array.

9. The method of claim 8, wherein the method further comprises the step of:
    heating at least one of the gas sensors in the array to a different temperature from another at least one or more of the gas sensors in the array.

10. The method of claim 8, wherein the method further comprises the step of:
    recording a time the readings are taken from the gas sensors to determine a path of a gas as the gas passes over the array.

11. A method of gas detection, the method comprising the steps of:
    providing a gas detector device having at least one gas sensor comprising: a plurality of fins; a conformal resistive heating element on the fins; a conformal barrier layer on the resistive heating element; and a conformal sensing layer on the barrier layer, wherein the conformal resistive heating element, the conformal barrier layer and the conformal sensing layer each conforms to a shape of the fins thereby providing a plurality of gas sensor layers disposed conformally over the fins with a gap present between the gas sensor layers over adjacent fins;
    heating the gas sensor via the resistive heating element; and
    taking readings from the gas sensor.

12. The method of claim 11, wherein the resistive heating element comprises a material selected from the group consisting of: tantalum nitride, titanium nitride, tungsten, and combinations thereof.

13. The method of claim 11, wherein the barrier layer comprises a material selected from the group consisting of: silicon nitride, silicon oxide, alumina, and combinations thereof.

14. The method of claim 11, wherein the sensing layer comprises a material selected from the group consisting of: tin oxide, zinc oxide, and combinations thereof.

15. The method of claim 11, wherein the gas sensor comprises multiple rows of the resistive heating element, the barrier layer, and the sensing layer interconnected in a serpentine configuration.

16. The method of claim 11, wherein the gas detector device comprises a plurality of gas sensors arranged in an array.

17. The method of claim 16, wherein the method further comprises the step of:
    heating at least one of the gas sensors in the array to a different temperature from another at least one or more of the gas sensors in the array.

18. The method of claim 16, wherein the method further comprises the step of:
    recording a time the readings are taken from the gas sensors to determine a path of a gas as the gas passes over the array.

* * * * *